(12) United States Patent
Ritzberger et al.

(10) Patent No.: US 8,034,264 B2
(45) Date of Patent: Oct. 11, 2011

(54) PROCESS FOR THE PREPARATION OF COLORED BLANKS AND DENTAL SHAPED PARTS

(75) Inventors: Christian Ritzberger, Nenzing (AT); Elke Apel, Sevelen (CH); Wolfram Höland, Schaan (LI); Frank Rothbrust, Frastanz (AT); Harald Kerschbaumer, Klaus (AT); Volker M. Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 819 days.

(21) Appl. No.: 11/802,053

(22) Filed: May 18, 2007

(65) Prior Publication Data

US 2007/0292597 A1 Dec. 20, 2007

(30) Foreign Application Priority Data

May 23, 2006 (DE) .......................... 10 2006 024 065
Sep. 13, 2006 (EP) ...................... 06120608
Mar. 8, 2007 (EP) ...................... 07004776

(51) Int. Cl.
*B05D 3/02* (2006.01)
*C04B 35/01* (2006.01)

(52) U.S. Cl. ............ 264/17; 264/113; 264/20; 264/245; 427/213; 118/303

(58) Field of Classification Search .................. 264/19, 264/20, 113, 122, 245; 118/303; 427/212–213
See application file for complete search history.

(56) References Cited

U.S. PATENT DOCUMENTS

| | | | |
|---|---|---|---|
| 3,984,524 A | 10/1976 | Alexandrov et al. | |
| 4,742,030 A | 5/1988 | Masaki | |
| 4,940,523 A * | 7/1990 | Takeshima | ............... 204/192.12 |
| 5,011,403 A | 4/1991 | Sadoun et al. | |
| 5,043,316 A | 8/1991 | Janssens | |
| 5,059,562 A * | 10/1991 | Gentsu | ............... 501/87 |
| 5,219,805 A | 6/1993 | Yoshida | |
| 5,263,858 A | 11/1993 | Yoshida et al. | |
| 5,308,243 A | 5/1994 | Emmons | |
| 5,656,564 A | 8/1997 | Nakayama et al. | |
| 5,800,164 A | 9/1998 | Pfau | |
| 6,030,209 A | 2/2000 | Panzera | |
| 6,254,757 B1 * | 7/2001 | Lashmore et al. | ............ 205/149 |
| 6,495,072 B1 | 12/2002 | Van der Zel | |
| 6,709,694 B1 | 3/2004 | Suttor | |
| 6,713,421 B1 | 3/2004 | Hauptmann | |
| 7,011,522 B2 | 3/2006 | Panzera et al. | |
| 7,686,989 B2 * | 3/2010 | Van der Zel | ............ 264/20 |
| 2002/0127130 A1 * | 9/2002 | Lashmore et al. | ............ 419/64 |
| 2003/0125189 A1 | 7/2003 | Castro et al. | |
| 2004/0152034 A1 | 8/2004 | Cummings et al. | |
| 2005/0023710 A1 | 2/2005 | Brodkin et al. | |
| 2005/0136096 A1 * | 6/2005 | Davidson | ............ 424/442 |
| 2007/0187185 A1 * | 8/2007 | Abraham et al. | ............ 187/288 |
| 2008/0206460 A1 * | 8/2008 | Rhoades et al. | ............ 427/192 |

FOREIGN PATENT DOCUMENTS

| | | |
|---|---|---|
| DE | 3418987 A1 | 11/1985 |
| DE | 199 04 522 A1 | 8/2000 |
| DE | 197 14 178 C2 | 9/2003 |
| EP | 0218853 A1 | 4/1987 |
| EP | 0 442 150 A2 | 8/1991 |
| EP | 1076036 | 2/2001 |
| EP | 0 955 267 B1 | 9/2003 |
| EP | 1 076 036 B1 | 10/2003 |
| EP | 1 354 567 A1 | 10/2003 |
| EP | 1076036 B1 | 10/2003 |
| EP | 1 400 232 A1 | 3/2004 |
| EP | 1400232 A1 | 3/2004 |
| EP | 1 210 054 B1 | 8/2004 |
| FR | 2 781 366 A1 | 1/2000 |
| JP | 2145476 | 6/1990 |
| JP | 3028161 | 2/1991 |
| JP | 5043316 | 2/1993 |
| JP | 08033650 | 6/1996 |
| JP | 2005289721 | 10/2005 |
| WO | WO 02/085242 A1 | 10/2002 |
| WO | WO 2007/053084 A1 | 5/2007 |

OTHER PUBLICATIONS

P. Duran, P. Recio, J.R. Jurado, C. Pascual and C. Moure, "Preparation, Sintering, and Properties of Translucent Er2O3—Doped Tetragonal Zirconia," J. Am. Ceram. Soc., vol. 72, No. 11, pp. 2088-2093, 1989.

M. Yashima, T. Nagotome, T. Noma, N. Ishizawa, Y. Suzuki and M. Yoshimura, "Effect of Dopant Species on Tetragonal to Monoclinic Phase Transformation of Arc-Melted ZrO2-RO15 (R=Sm, Y, Er, and Sc) in Water . . . " J.Am. Ceram. Soc., No. 78, No. 8,pp. 2229-2293, 1989.

K.C. Shah, I. Dnery and J.A. Holloway, "Physical Properties of Cerium-Doped Tetragonal Zirconia," Abstract 0080, Journal of Dental Research, Vo. 85, Special Issue A, 2006.

* cited by examiner

*Primary Examiner* — Joseph Del Sole
*Assistant Examiner* — Nahida Sultana
(74) *Attorney, Agent, or Firm* — Ann M. Knab

(57) ABSTRACT

The invention relates to compositions based on $ZrO_2$, and single- and multi-colored blanks made from oxide ceramics, and a process for their preparation, in which oxide ceramic powder is coated with a coloring substance, the coated powders are preferably graded and at least one colored powder is filled into a compression mould, the colored powder or powders are compressed to produce a shaped body, and the compressed shaped body is sintered to produce a blank, and to the use of these blanks for the preparation of dental restorations.

26 Claims, No Drawings

PROCESS FOR THE PREPARATION OF COLORED BLANKS AND DENTAL SHAPED PARTS

This application claims priority pursuant to 35 U.S.C. §119, to German Patent Application No. 10 2006 024 065.0 filed May 23, 2006, and European Patent Application Nos. 06120608.2 filed Sep. 13, 2006, and 07004776.6 filed Mar. 8, 2007, the entire contents of which are incorporated herein by reference.

FIELD

The present invention relates to single- or multi-colored shaped bodies, blanks and dental shaped parts made from oxide ceramics, a process for their preparation, their use for the preparation of dental restoration shaped parts and also a composition which is particularly suitable for their manufacture.

BACKGROUND

In the discussion that follows, reference is made to certain structures and/or methods. However, the following references should not be construed as an admission that these structures and/or methods constitute prior art. Applicants expressly reserve the right to demonstrate that such structures and/or methods do not qualify as prior art.

The use of oxide ceramics as a framework material for dental restorations has long been state of the art. This material is characterized by an excellent biocompatibility and outstanding mechanical properties. For many years it has also been widely used as an implant material and for prostheses. In the past few years, ceramics based on partially stabilized $ZrO_2$ ceramics have been used in particular.

The shaping of these ceramics in dental engineering is typically performed by mechanical means. In particular, milling of partially sintered ceramics with CAD/CAM processing units has gained acceptance. The shrinkage which occurs during final densification of shaped bodies, going from a density of approximately 40-60% to a density of more than 95%, is taken into account during the mechanical processing. The quoted density is relative to the theoretical density.

The disadvantages of $ZrO_2$ ceramics are the low translucency and their milky-white color. A non-colored and non-coated restoration or restoration part looks like an unnatural tooth. Coloring the $ZrO_2$ ceramic to match the patient's situation for an aesthetic tooth reconstruction are thus essential.

A particularly great disadvantage of sintered ceramics according to the state of the art is that they do not produce blanks for CAD/CAM processing in open-pored form or in dense-sintered form which are multi-colored or have zones of different colors corresponding to the coloration of a natural tooth.

All that is known from the state of the art is a series of technical solutions for colored, not multi-colored, blanks. However, these solutions have the disadvantage that the natural tooth color, the color gradient, the polychromatism, the graduated translucency and brightness of color were not achieved. These known solutions are described as follows:

The preparation of an open-porous colored and white $Y_2O_3$-containing $ZrO_2$ blank is achieved according to EP 1 210 054 from liquids via co-precipitation from chlorides which contain Zr, Y, Al, Ga, Ge, In, Fe, Er and Mn ions. By means of the co-precipitation and subsequent calcination, the prepared powder already contains the coloring ions before shaping. Oxides from the group $Fe_2O_3$, $Er_2O_3$ and $MnO_2$ are selected as coloring compounds. The disadvantage of this approach is that a very costly and laborious method of the co-precipitation process with subsequent calcination must be carried out in order to obtain a colored powder. This means that this process must be carried out for every single color.

In the following disclosures monolithic ceramics are presented which each allow one specific color, thus polychromatism, is not achieved.

U.S. Pat. No. 5,263,858 (Yoshida et el.) describes the preparation of ivory-colored shaped bodies for dental applications (brackets), wherein during the preparation of the stabilized $ZrO_2$ ceramic coloring compounds in solutions are added before the calcination, or as powdery mixtures of coloring oxides after the calcination. In order to achieve the desired ivory shade, the addition of $Fe_2O_3$, $Pr_6O_{11}$ and $Er_2O_3$ is necessary. However, this process has the disadvantage that it is a multi-stage process.

It is further known from the state of the art according to FR 2 781 366 to mix the coloring components with the starting powder of the $ZrO_2$, grind and sinter jointly. $Fe_2O_3$, $CeO_2$ and $Bi_2O_3$ are mentioned as coloring oxides.

EP 0 955 267 mentions contents of 5-49 wt.-% $CeO_2$, whereby coloration is achieved.

For the preparation of completely cubically stabilized zirconium dioxide in an arc-furnace process, according to EP 1 076 036 B1 one or more stabilizing and coloring oxides or their precursors are added to a $ZrO_2$ source. The coloring oxides of the elements Pr, Ce, Sm, Cd, Tb are inserted into the crystal lattice of the $ZrO_2$ after the sintering process.

U.S. Pat. No. 5,656,564 relates to the preparation of zirconium oxide shaped bodies which contain oxides of the rare earths boron oxide, aluminum oxide and/or silicon oxide. The shaped bodies contain zirconium dioxide as a mixed phase of tetragonal and monoclonal $ZrO_2$. Oxides of the elements Pr, Er and Yb are introduced into the sintered ceramic as coloring oxides.

Technical solutions are further known according to the state of the art which allow colored blanks to be obtained by infiltration of liquids. However, these technical solutions have the serious drawback that coloring takes place after the pre-sintering process, and thus liquids are introduced into an open-porous ceramic body. The coloring is not completely homogeneous and also a multi-coloration cannot be achieved.

Unlike sintered ceramics, such as $ZrO_2$ and $Al_2O_3$, a process for the preparation of multi-colored glass ceramic blanks is known from DE 197 14 178 C2. However, the preparation of multi-colored $ZrO_2$ blanks is not mentioned in this document.

A disadvantage of the state of the art is that multi-colored sintered ceramic blanks cannot be prepared. Moreover, the solutions according to the state of the art are very costly and quality problems arise. The latter applies to the infiltration technique. Due to the subsequent coloring of a partially sintered blank or of a shaped dental product only the voids (pores) between the partially sintered particles of the starting powder can be occupied by the coloring ions. As a result, only discrete areas of the surface of the particles are colored with a layer of the coloring oxides, a continuous coverage of the surface of the particles of the starting powder not being possible. A further great disadvantage with infiltration is the concentration gradient of the coloring from the outside inwards. If a porous body is introduced into the coloring solution, the starting solution releases part of the dissolved coloring ions, starting from the outside inwards, and thus the coloring solution is "depleted" of some of its coloring substances. The consequence of this is that there is a higher concentration of the coloring ions on oxides outside than in the inside of the shaped body. Furthermore, only a certain depth of penetration can be achieved by means of the infiltration technique.

SUMMARY

An object of the invention is to avoid one or more disadvantages of the state of the art described above, and to prepare an oxide powder that contains the coloring compounds uniformly distributed therein and is suitable for further processing to form a dental restoration part from this uniformly colored oxide powder, as well as a shaped body, an open-pored blank and a dental shaped part, which also contain the coloring compounds uniformly distributed therein.

A further object of the invention is to provide single- or multi-colored shaped parts, blanks and dental shaped parts which contain the coloring compounds in a gradient or zones.

The first object of the invention is achieved by processes in which a) an oxide powder is coated with a coloring substance,
b) the coated powder is optionally graded and optionally filled into a compression mould,
c) the colored powder is compressed to give a shaped body and
d) the compressed shaped body is sintered to produce a blank, and
e) optionally the dental shaped part is formed therefrom.

A further object of the invention is achieved by single- and multi-colored shaped bodies, blanks and dental shaped parts, made from colored oxide ceramic powder or from colored oxide ceramic powder and uncolored oxide ceramic powder, which have a ratio of the oxide ceramic component to the coloring oxide, or of the mixtures of coloring oxides, in parts by weight of 100:0.0001 to 2.0.

As used herein "layer" means an individual component which produces a single-colored shaped body, blank or dental shaped part. The term "layers" illustrates the course or variation of the color as a color gradient or zones of a multi-colored shaped body, blank or multi-colored dental shaped part.

The invention also relates to the use of the single- or multi-colored shaped body, blank or dental shaped part for the preparation of dental restoration parts.

The invention further relates to a composition based on $ZrO_2$ which can be processed with very small quantities of coloring substances to produce dental restorations closely resembling natural teeth.

DETAILED DESCRIPTION

With the processes according to the invention, the coloring of the oxide ceramic takes place before the compression of the blanks and thus before the pre-sintering or sintering process. For the preparation of multi-colored shaped bodies, blanks or dental shaped parts, coating can be carried out with further coloring substances. For this, in a first step a first coloring substance is applied onto an uncolored oxide ceramic powder. In a second step, the next coloring substance is then applied onto further uncolored oxide ceramic powders. Depending on the number of desired colors, in several further steps a further coloring, with further coloring substances may be applied on further uncolored oxide ceramic powders. The result is oxide powder particles containing different color compounds.

Coating with the coloring substances can be carried out in a fluidized-bed reactor. Other coating methods known to a person skilled in the art can also be used according to the invention.

Suitable fluidized-bed methods are known from other fields of the art. These methods have not yet been used for the coloring of oxide ceramic powders which are used in the dental field. A material, loosened by a carrier medium (gas or liquid) of fine-grained solid particles is moved in the fluidized bed (also called fluid bed). For this, a gas flows from bottom to top through a stationary packing comprising oxide ceramic powder with an average grain diameter of the granules of 1 to 100 μm, preferably 30 to 80 μm. At a specific rate of flow (loosening point, fluidizing point) the packing transforms into the fluidized bed. Powders with the given average granule diameter are therefore preferred. Either the bottom spray or the top spray method can be used during the fluidized coating.

As the fluidized bed forms, the weight of the solid particles is neutralized by the oppositely-directed flow force of the carrier medium. The solid then behaves similarly to a liquid, i.e. it can be easily supplied or removed during the operation. A very intensive material and heat exchange takes place in the fluidized bed. Consequently, a coloring of the oxide ceramic powders can be achieved according to the invention by using a fluid which contains coloring substances.

Oxidic sintered ceramics, such as $ZrO_2$ powders, can be used as oxide ceramic powders As used herein, "sintered ceramics" means products which are produced from crystalline raw materials in a heat treatment process by sintering, wherein the crystal portion is very largely retained and only a small portion, in most cases well below 5 vol-% glass phase portion, forms between the individual crystals.

According to the invention the $ZrO_2$ can also be doped with further metal oxides. For example, doping with $CeO_2$, $Y_2O_3$, MgO or CaO is possible. $HfO_2$ and $Al_2O_3$ can also be contained in the $ZrO_2$ powder.

The oxides of the d- and f-elements of the periodic table of the elements can be used as coloring oxides. The coloring oxides $Pr_2O_3$, $Fe_2O_3$, $Tb_2O_3$ and/or $Cr_2O_3$ and further oxides can be used for this.

$Pr_2O_3$, $Fe_2O_3$ and $Tb_2O_3$ are used as coloring oxides according to certain aspects of the present invention.

Oxides of the elements Mn, V, Ti, Nd, Eu, Dy, Er and/or Yb, in particular oxides of Mn, can be used as further coloring oxides.

Aqueous solutions of various salts can be used as coloring substances. Water-soluble salts of d- or f-elements of the periodic table can be utilized. Nitrate or chloride hydrates of these elements are particularly examples. Examples of salts that can be used are $Pr(NO_3)_3 \cdot 5H_2$, $Fe(NO_3)_3 \cdot 9H_2O$ or $Tb(NO_3)_3 \cdot 5H_2O$.

In addition to the coloring substances, suitable water-soluble binders can also be used as compression aids for the powder. The binders can be dissolved with the above-mentioned salts in water and homogenized. Polyvinyl alcohol is one exemplary binder.

According to further embodiments a surfactant can be added to the powder, as this surprisingly improves compressibility. This is shown by a higher compression density at the same pressure. Non-ionic or amphoteric surfactants, such as polyglycol ethers or alkyl sulphonates, can be utilized.

The oxide ceramic powders coated with the coloring substances are preferably graded, e.g. screened using sieves with a mesh width of <90 μm, in a second step. Grading may be performed when there is agglomeration of the powder.

The optionally graded powder is then normally introduced into a compression mold. If the preparation of multi-colored blanks is intended, the first process step described above is carried out several times with other coloring substances or at higher concentrations of the coloring substances, with the result that differently colored powders are produced. In a second step these differently colored powders are poured portionwise into a compression mold after the grading.

Compression, such as cold isostatic pressing, of a shaped body is carried out at pressures of 50 to 500 MPa, particularly at 70 to 300 MPa, quite particularly at 100 to 200 MPa. According to the invention a uniaxial compression is also possible.

In a further process step the obtained shaped body is sintered, in particular pre-sintered. Temperatures of 800 to 1300° C., particularly 1000° C. to 1200° C., quite particularly of 1050° C. to 1150° C., are used for this. A porous blank with a density of at least 30%, particularly 40 to 75% of the theoretical density of the oxide ceramic is obtained by the pre-sintering process. The duration of the pre-sintering at the given temperatures is 1 to 4 hours, particularly 1.5 to 2.5 hours. The complete pre-sintering step including heating and cooling processes usually lasts 38 to 72 hours.

Debindering of the shaped body takes place at the same time during the pre-sintering process. "Debindering" means the burning out of the organic constituents, in particular the binders. However, this debindering can also be carried out in a separate process step.

The obtained single- or multi-colored blank is shaped into a dental shaped part for example in a dental laboratory or dental clinic. This can take place by milling or grinding by means of a CAD/CAM unit. The thus-obtained enlarged preform of a dental shaped part of the dental restoration is then densely-sintered at a temperature of 1200° C. to 1600° C., particularly 1300° C. to 1550° C. and quite particularly 1400° C. to 1500° C. The duration of the dense sintering step lasts 5 minutes and 2 hours, particularly 10 to 30 minutes. The complete dense-sintering process with heating and cooling generally lasts approximately 8 hours. The milling process is carried out such that the dental shaped part displays an excess that takes into account the shrinkage of the shaped part during the dense sintering.

The dense sintering can also be carried out using microwave energy, which as a rule leads to a shortening of the process times.

The prepared dental shaped part can represent the finished dental restoration, or can be processed further, such as provided with a veneer in order to produce the finished dental restoration.

The dental shaped parts prepared in the way described are characterized, unlike the dental shaped parts previously known from the state of the art, by a high color homogeneity. The coloring ions are present in aqueous phase and are applied homogeneously to the surface of the oxide ceramic powders, in particular in the fluidized bed. Even at very low concentrations of about 0.001 wt.-%, relative to the total amount of powder, a homogeneous coating of the powder is obtained. It is also advantageous according to the invention that mixed colors may be obtained, and blanks can be prepared in multi-colored form.

The invention contemplates the use of multi-colored blanks of the $ZrO_2$ ceramic, that after dense sintering, there is a multi-colored product for restorative dental medicine. This polychromatism is extremely advantageous, quite particularly for multi-span bridges. Thus natural tooth coloration can be perfectly reproduced by such a dental restoration, as the latter does not consist of just one color, but has a color gradient and translucency differences as well as different color brightnesses within the tooth. If a multi-colored bridge according to the invention is now prepared, these aforementioned requirements or properties of a natural tooth can be easily ensured. This ease of preparation of dental shaped parts, e.g. of complicated dental restorations, such as multi-span bridges, is obtainable according to the invention by the fact that the dental technician needs to apply only a few sintered ceramic or sintered glass ceramic veneer layers, or even just one, to the multi-colored ceramic bridge in order to achieve the most natural look. Several layers have to be applied to uncolored ceramics as a veneer and in order to achieve special color effects. Various sinterings are also necessary in case of single-colored ceramics. Operations according to the invention are therefore more effective than according to the state of the art.

A further advantage is that a uniform distribution of pores is not a precondition for coloration. The infiltration technique depends on as uniform as possible a distribution of the pores in order to obtain colorings that are acceptable to at least some extent. Accordingly, wholly different coloring qualities are obtained according to the state of the art because of different roughness and inaccessible pores.

It is furthermore advantageous according to the invention that, with the coloring according to the invention of the oxide ceramic powders through the homogeneous distribution of the coloring substances on the surface of the powders or of the agglomerates thereof, no accumulation of the coloring substances occurs. An imperfection in the structure is thereby reliably avoided. If the process described above is carried out with differently colored oxide ceramic powders, the result after the compression, debindering and sintering is a multi-colored blank which has a color gradient which preferably corresponds to that of a natural tooth.

Furthermore, grain growth within the ceramic is not negatively influenced during sintering. The color ion distribution is so favorable that neither color gradients nor accumulations of color ions are visible or analyzable with either the human eye or with a scanning electron microscope (SEM) or a transmission electron microscope (TEM).

Finally, a process performed according to the invention in which the blank or the dental shaped part or the dental restoration prepared therefrom contains a composition according to the invention that is described below.

A composition according to the invention is based on $ZrO_2$, and contains the following components:
Pr, calculated as $Pr_2O_3$,
Fe, calculated as $Fe_2O_3$,
Tb, calculated as $Tb_2O_3$, and
Mn, calculated as $Mn_2O_3$,
in a total quantity of 0.0001 to 0.75 wt.-%.

Surprisingly, it was shown that such a composition, despite the very small total quantity of coloring components, namely Pr, Fe, Tb and Mn, allows the preparation of blanks, dental shaped parts and finally dental restorations which are intensely colored in the desired way in order to excellently imitate the natural tooth material.

The components Pr, Fe, Tb and Mn can be present in different oxidation stages in the composition, preferably being present in an oxidation stage other than zero.

It is assumed that during the preparation of the composition by the above-given process according to the invention, in particular after pre-sintering or dense-sintering steps have been carried out, an insertion of the components in the form of ions into the crystal lattice of the $ZrO_2$ takes place. For example, it is possible that these ions are inserted into defects of the $ZrO_2$ lattice.

The composition is therefore preferably present in sintered form. In addition it contains the given components preferably homogeneously distributed.

It is further preferred that the composition contains the components in a total quantity of 0.0001 to 0.6 wt. % and in particular 0.0004 to 0.37 wt.-%.

Furthermore, a composition which contains the components in the following quantities has proved particularly effective:

| Component | Quantities (wt.-%) |
|---|---|
| Pr, calculated as $Pr_2O_3$ | 0.0001-0.01 |
| Fe, calculated as $Fe_2O_3$ | 0.005-0.5 |
| Tb, calculated as $Tb_2O_3$ | 0.0001-0.1 |
| Mn, calculated as $Mn_2O_3$ | 0.0001-0.1 |

In addition, particular ranges may also exist for the individual components as follows:

Pr, calculated as $Pr_2O_3$, in a quantity of 0.0005 to 0.01 wt.-%

Fe, calculated as $Fe_2O_3$, in a quantity of 0.005 to 0.4 wt.-%

Tb, calculated as $Tb_2O_3$, in a quantity of 0.0001 to 0.075 wt.-%

Mn, calculated as $Mn_2O_3$, in a quantity of 0.0001 to 0.075 wt.-%

Finally, it was surprisingly shown that special compositions can be very advantageously used as basic colors in the preparation of dental restorations. Four specific embodiments are described below of the composition according to the invention, giving the contained quantities of the components:

| Component | Quantities (wt.-%) |
|---|---|
| Pr, calculated as $Pr_2O_3$ | 0.001-0.003 |
| Fe, calculated as $Fe_2O_3$ | 0.005-0.04 |
| Tb, calculated as $Tb_2O_3$ | 0.0005-0.004 |
| Mn, calculated as $Mn_2O_3$ | 0.0001-0.0005 |
| Pr, calculated as $Pr_2O_3$ | 0.002-0.004 |
| Fe, calculated as $Fe_2O_3$ | 0.04-0.15 |
| Tb, calculated as $Tb_2O_3$ | 0.0005-0.004 |
| Mn, calculated as $Mn_2O_3$ | 0.0003-0.002 |
| Pr, calculated as $Pr_2O_3$ | 0.003-0.006 |
| Fe, calculated as $Fe_2O_3$ | 0.04-0.15 |
| Tb, calculated as $Tb_2O_3$ | 0.0005-0.004 |
| Mn, calculated as $Mn_2O_3$ | 0.0005-0.002 |
| Pr, calculated as $Pr_2O_3$ | 0.003-0.006 |
| Fe, calculated as $Fe_2O_3$ | 0.04-0.25 |
| Tb, calculated as $Tb_2O_3$ | 0.0005-0.004 |
| Mn, calculated as $Mn_2O_3$ | 0.001-0.007 |

Compositions according to the invention can contain further substances, such as Cr, calculated as $Cr_2O_3$, in a quantity of 0.0001 to 0.1 wt.-%

Furthermore, it is advantageous if the composition includes a stabilizer such as $Y_2O_3$. Compositions which contain 4 to 8 wt.-% $Y_2O_3$ represent specific embodiments.

Compositions may also contains up to 1 wt.-% $Al_2O_3$. This increases the stability of the composition according to the invention under hydrothermal conditions, which is of particular importance when using the composition according to the invention as a dental material. The composition can also contain $HfO_2$.

Compositions which contains more than 95 wt/%, in particular more than 98 wt.-% $ZrO_2$ are contemplated. Compositions in which the $ZrO_2+HfO_2+Y_2O_3$ content of the composition is more than 95 wt.-% are also contemplated.

Compositions according to the invention can be used in particular as dental material. Compositions according to the invention can in particular be prepared by a process in which a powder based on $ZrO_2$ is coated with a source of the components, such as compounds of Pr, Tb, Fe and Mn, in particular by means of fluidized bed coating.

Finally, the invention also relates to a shaped body which contains the composition according to the invention and particularly those which have a homogeneous distribution of the components Pr, Tb, Fe and Mn within the whole body and thus an excellent color homogeneity. This shaped body is present in particular as a blank, dental shaped part or dental restoration, i.e. preferably as a sintered shaped body. The shaped body according to the invention can be produced in particular by the above-given process according to the invention for the preparation of blanks and dental shaped parts.

Blanks according to the invention can be provided with a density of 3.0 to 3.5 g/cm$^3$, in particular 3.1 to 3.2 g/cm$^3$.

A shaped body is further preferred which is multi-colored, wherein the polychromatism is brought about in particular by several differently colored layers. Shaped bodies which have at least two differently colored layers and preferably contain up to eight differently colored layers have proved particularly advantageous.

The natural tooth material can be very well imitated by just such a shaped body, such as, e.g., a blank, with at least three differently colored layers. The natural tooth material can be roughly divided into three regions, namely cervical, central and incisal, each having different requirements with regard to visual appearance. Thus the appearance of one layer is preferably matched to the cervical, and the appearance of the other two layers preferably matched to the central and incisal regions of the natural tooth. It has also proved particularly advantageous if at least one layer of the body contains a composition according to the invention and in particular a composition of the above-mentioned four special embodiments of the invention. Moreover, it is also possible that this at least one layer contains a mixture of the above-given four special embodiments and thus the basic colors represented by these embodiments can be modified.

A comparison with conventional colored compositions based on $ZrO_2$ has shown that the special components of the compositions according to the invention, even in very small quantities, allow a desired color intensity to be obtained. The conventional system frequently requires a much greater quantity of coloring components for this, which leads to imperfections in the structure of the bodies produced therefrom. The comparatively small quantities of coloring components used in the case of the compositions according to the invention essentially cause no imperfections in the structure of the bodies produced therefrom, with the result that they and in particular the dental restorations that are finally prepared have excellent physical properties, such as strength and chemical stability.

Finally therefore the invention also relates to the use of the composition according to the invention or of the body according to the invention for the preparation of dental restorations. The dental restoration is in particular a crown and quite particularly preferably a bridge. It is of particular importance in particular with a bridge if the different colors present in the natural teeth that are to be replaced can be imitated as faithfully as possible. However, this is possible in an excellent way with the composition according to the invention and the shaped bodies prepared therefrom, through the provision of correspondingly differently colored regions, such as differently colored layers.

The invention is explained in more detail below by means of the following illustrative, non-limiting examples.

EXAMPLES

All the optical values L, a and b given within the framework of the examples were determined in accordance with the standards DIN 5033 or DIN 6174, by carrying out a comparison with a white reference sample with the values $L^*=93.11$, $a^*=0.64$ and $b^*=4.22$. The value C represents the vector sum of a and b. Color measurement was carried out by means of a Konica-Minolta CM-3700d spectrometer. The CR value was determined in accordance with the standard BS 5612 and is a measure of opacity.

Partially stabilized $ZrO_2$ powders, e.g. TZ-$_3$Y or TZ-$_3$YSB-C, from the company Tosoh which had the compositions below were used as starting material for compositions according to the invention and shaped bodies, blanks and dental shaped parts prepared therefrom:

| | |
|---|---|
| $ZrO_2 + HfO_2 + Y_2O_3$ | >99.0 wt.-% |
| $Y_2O_3$ | 4.5-5.4 wt.-% |
| $HfO_2$ | ≦5.0 wt.-% |
| $Al_2O_3$ | 0.2-0.5 wt.-% |
| Other oxides | ≦0.5 wt.-% |
| Radioactivity | <200 Bq kg$^{-1}$ |
| Bulk density | 3.09-3.21 g/cm$^3$ |

An aqueous solution which contained both the coloring ions and a water-soluble binder, such as polyvinyl alcohol (e.g., Optapix PAF2 or PAF35 from the company Zschimmer & Schwarz) was used as a coloring solution for the fluidized-bed coating. The coloring solution can contain one or more coloring ions in order to achieve the desired coloration after the dense sintering. The aqueous coloring solution with about 0.1-2 wt.-% binder (relative to the quantity of powder to be coated) contained the respective coloring ions. This solution was homogenized for approximately half an hour (magnetic stirrer or the like). This coloring solution was then applied completely by means of a fluidized-bed granulator on the uncolored $ZrO_2$ powder. During this step the powder to be coated was kept in suspension (fluidized bed) by means of compressed air (0.15-0.30 bar) and at the same time the coloring solution was sprayed through a nozzle, which was arranged above this fluidized bed, and applied to the powder. The spraying pressure here was between 2 to 6 bar. In addition, the compressed air which was necessary to maintain the fluidized bed was heated to approximately 30 to 80° C., and was thus able to dry the powder at the same time during the process.

Preparation of a Single-Colored $ZrO_2$ Blank $ZrO_2$ powder (TZ-3YSB-C) was coated with an aqueous coloring solution based on Fe(III), Pr, Cr and Tb compounds. The thus-colored powder was introduced into a compression mould and subjected to cold isostatic compression at about 200 MPa. This shaped body was then pre-sintered at a temperature of 1125° C. over a period of about 120 min. to produce a blank and then worked by means of CAD/CAM technology. It was then dense-sintered at about 1500° C. The dental shaped part had a slightly yellowish color after the dense sintering. Square blanks were preferably prepared which preferably had the following measurements:

| | |
|---|---|
| Length | about 15 to about 60 mm |
| Width | about 10 to about 20 mm |
| Height | about 15 to about 20 mm |

The preparation of cylindrical blanks was, however, also possible. The crystallite size, analyzed by means of SEM, of the partially sintered blank was about 200 to 400 nm. The crystallite size in the densely sintered restoration was about 400 to 800 nm.

The following TABLE I gives the compositions of differently colored blanks according to Examples 1 to 10 together with the optical values after dense sintering. The levels of the components are expressed as levels of the respective trivalent oxide. $ZrO_2$ powders from Tosoh, Japan, containing 4-8 wt.-% $Y_2O_3$ were used as starting material. The powders differed in their primary particle size, specific surface and binder content. These powders were provided as described above with the coloring components.

TABLE I

| Example | Composition (TZ-3Y, TZ-3YSB or TZ-3YSB-E) + following components | Optical values | | | | | Optical appearence |
|---|---|---|---|---|---|---|---|
| | | L* | a* | b* | C* | CR | |
| 1 | 0.05 wt.-% $Pr_2O_3$<br>0.0001 wt.-% $Cr_2O_3$<br>0.001 wt.-% $Fe_2O_3$<br>0.0001 wt.-% $Tb_2O_3$ | 84.02 | 2.37 | 25.74 | 25.85 | 94.33 | yellowish |
| 2 | 0.1 wt.-% $Cr_2O_3$<br>0.0001 wt.-% $Tb_2O_3$<br>0.0001 wt.-% $Pr_2O_3$<br>0.001 wt.-% $Fe_2O_3$ | 63.30 | 1.78 | 5.22 | 5.51 | 98.10 | dark grey |
| 3 | 0.1 wt.-% $Fe_2O_3$<br>0.0001 wt.-% $Cr_2O_3$<br>0.0001 wt.-% $Pr_2O_3$<br>0.0001 wt.-% $Tb_2O_3$ | 81.39 | 1.80 | 17.23 | 17.33 | 97.97 | reddish-brown |
| 4 | 0.072 wt.-% $Fe_2O_3$<br>0.003 wt.-% $Cr_2O_3$<br>0.003 wt.-% $Pr_2O_3$<br>0.0001 wt.-% $Tb_2O_3$ | 79.19 | 1.87 | 18.64 | 18.74 | 99.47 | reddish-brown (tooth color) |
| 5 | 0.0001 wt.-% $Pr_2O_3$<br>0.0001 wt.-% $Mn_2O_3$<br>0.0001 wt.-% $Fe_2O_3$<br>0.05 wt.-% $Tb_2O_3$ | 84.23 | 1.61 | 22.95 | 23.00 | 96.07 | yellowish |
| 6 | 0.0001 wt.-% $Pr_2O_3$<br>0.1 wt.-% $Mn_2O_3$<br>0.0001 wt.-% $Fe_2O_3$<br>0.0001 wt.-% $Tb_2O_3$ | 51.48 | 2.49 | −1.71 | 3.02 | 95.02 | anthracite |
| 7 | 0.0040 wt.-% $Pr_2O_3$ | 86.87 | −0.52 | 10.40 | 40.42 | 92.49 | slightly |

TABLE I-continued

| Example | Composition (TZ-3Y, TZ-3YSB or TZ-3YSB-E) + following components | L* | a* | b* | C* | CR | Optical appearence |
|---|---|---|---|---|---|---|---|
| 8 | 0.0001 wt.-% $Mn_2O_3$<br>0.001 wt.-% $Fe_2O_3$<br>0.0001 wt.-% $Tb_2O_3$<br>0.001 wt.-% $Pr_2O_3$ | 72.24 | 6.10 | 22.10 | 22.92 | 98.59 | yellowish<br>yellow-brown |
| 9 | 0.0001 wt.-% $Mn_2O_3$<br>0.5 wt.-% $Fe_2O_3$<br>0.0001 wt.-% $Tb_2O_3$<br>0.0006 wt.-% $Pr_2O_3$ | 89.94 | −0.20 | 5.05 | 5.05 | 96.70 | cream-white |
| 10 | 0.0001 wt.-% $Mn_2O_3$<br>0.0002 wt.-% $Fe_2O_3$<br>0.0001 wt.-% $Tb_2O_3$<br>0.05 wt.-% $Pr_2O_3$<br>0.1 wt.-% $Mn_2O_3$<br>0.5 wt.-% $Fe_2O_3$<br>0.05 wt.-% $Tb_2O_3$ | 53.09 | 1.54 | 4.35 | 4.62 | 99.49 | anthracite |

Example 11

Preparation of a Multi-Colored Blank Based on $ZrO_2$

Differently colored powders (different tooth colors) were homogeneously poured successively into a compression mould according to the desired layer thickness and color transition. The powder was subjected to cold isostatic compression at approximately 200 MPa and then pre-sintered at 1125° C. for about 120 min. A preform of a dental shaped part was then produced from the blank and dense-sintered. The dental shaped part was then cut open lengthwise, and a color gradient was seen which cannot be thus prepared by means of the infiltration technique. This natural color gradient, thus the reproduction of the visual properties of the natural tooth, became clear in particular in the case of a 3-span side-tooth bridge. Using the blank according to the invention, it proved possible to reconstruct the natural color transition without an additional coating technique in the dense-sintered dental shaped part. The color transition of a side-tooth bridge according to the invention is characterized in that a higher chroma (a more intense color) is realized in the fissure and at the neck of the tooth than in the area of the cusps of the tooth. A much better aesthetic was obtained compared with the substances and materials of the state of the art. Furthermore, the time spent by the dental technician on the preparation of the completely coated restoration was able to be reduced.

Aqueous systems with soluble ionogenic compounds, preferably chlorides and nitrates, were used as coloring solutions.

Blanks with a color transition comprising, e.g., 2 up to 10 colors, were able to be produced in a large homogeneity as single- and multi-colored blanks with this process.

Example 12

Comparative Example According to the State of the Art

A 3-span bridge framework was ground from an IPS e.max ZirCAD® bridge block in a CAD/CAM unit (Sirona inLab®). The shrinkage factor of approximately 20% per space axis was taken into account by a corresponding enlargement ratio during grinding. The grinding process was carried out wet, with the result that the framework had to be dried before the infiltration process. The drying was carried out over 2 hours at about 80° C. under an infrared lamp. The reworked frameworks (removal of handpiece and regrinding of the edges) were infiltrated with the following solutions for the coloring (values in wt.-%), in order to ascertain differences in the color homogeneity:

TABLE II

| Solution | $Fe(NO_3)_3 \cdot 9H_2O$ | $H_2O$ | PEG 20000 | Ethanol |
|---|---|---|---|---|
| 1 | 4.2 | 76.6 | — | 19.2 |
| 2 | 4.8 | 54.4 | 27.2 | 13.6 |

PEG 20000: Polyethylene glycol (Flucka, Buchs, Switzerland)

A bridge framework was immersed for 2 min. in solution 1, infiltration taking place by capillary action. The use of a vacuum or above-atmospheric pressure was dispensed with. After the infiltration the framework was removed from the solution and dabbed dry by means of a paper towel in order to remove the excess coloring solution from the surface. The drying followed under an infrared lamp at 80° C. for approximately 2 hours. Already at this point in time a concentration of the Fe ions at exposed points of the framework (e.g., framework cusps of the masticating surface, high surface curvature) revealed itself. Even after the dense sintering at 1500° C. for 30 min. the color inhomogeneity resulting therefrom was clearly visible. A uniform outer coloring was not realizable.

A further bridge framework was dipped into coloring solution 2 for 2 min. to improve the color homogeneity. Post-treatment took place as described above. It was shown that the disadvantage of the superficial color inhomogeneity was able to be dealt with by the addition of the organic component and thus an increase in the viscosity of the coloring solution. The sintering also took place as described above. However, after the bridge framework was sectioned along the longitudinal axis it was shown that the coloring had taken place only in the outer layer zone of about 0.6 to 1.0 mm and thus there was not homogeneous coloring within the whole framework. This is possibly sufficient for an abutment crown, but there are major doubts in the area of the connectors and of the intermediate section of the bridge. During a subsequent grinding by the dental technician there is the danger that uncolored areas will be partially exposed and the originally intended effect of a coloring will be lost.

The comparative example shows that when infiltration is used as a coloring process only a superficial coloring can be achieved or a complete thorough coloring is achieved with only inhomogeneous coloring varying locally in strength (concentration of the color ions). These disadvantages are avoided according to the invention. A homogeneous coloring of the whole blank is always to be recorded.

It has also proved advantageous if nanoscale $ZrO_2$ powder is used as starting material (primary particle size between 5 and 50 nm and a specific surface of >100 $m^2/g$) for the preparation of the blocks. After working to produce a bridge framework this shows a clearly reduced temperature during the dense sintering. Thus, depending on the materials used, temperatures of below 1250° C. were reached, which allows a dense sintering in customary dental firing furnaces. To prepare colored blocks (single- and multi-colored) the colored powders used above were added as a so-called color concentrate to the nanoscale $ZrO_2$ powder in a proportion of 0.0001 to 2.0 wt.-%. A temperature change during the dense sintering is not necessary.

Examples 13 to 17

Further particularly preferred compositions according to the invention were prepared in the manner given above for Examples 1 to 10 and further processed into blanks, dental shaped parts and dental restorations. The portions of the components, calculated as the respective trivalent oxide, and also the total portion of these color components and the presence of an additive possibly present during the compression into shaped bodies are listed in Table III below. The proportions are given as mg of component per kg of the whole composition.

The surfactant was polyglycol ether or alkyl sulphonates.

These compositions and in particular those according to Examples 13 and 17 can be used as typical dental colors. Surprisingly, despite the very small quantities of coloring components, these compositions can be processed into intensely colored dental restorations, such as in particular crowns and bridges.

The optical properties of colored dense-sintered blanks prepared from them are listed in Table IV below.

TABLE III

| Example | $Fe_2O_3$ mg/kg | $Pr_2O_3$ mg/kg | $Tb_2O_3$ mg/kg | $Mn_2O_3$ mg/kg | Total portion color comp. mg/kg | Additives |
| --- | --- | --- | --- | --- | --- | --- |
| 13 | 329 | 15 | 7 | 1 | 352 | Optapix PAF35 |
| 14 | 1 | 1 | 1 | 1000 | 1003 | Surfactant |
| 15 | 5000 | 10 | 1 | 1 | 5012 | Surfactant |
| 16 | 1 | 1 | 500 | 1 | 503 | Surfactant |
| 17 | 1000 | 25 | 6 | 10 | 1041 | Surfactant |

TABLE IV

| Example | L | A | b | C | CR |
| --- | --- | --- | --- | --- | --- |
| 13 | 87.76 | −1.02 | 10.22 | — | 94.62 |
| 14 | 51.48 | 2.49 | −1.71 | 3.02 | 95.02 |
| 15 | 72.24 | 6.10 | 22.10 | 22.92 | 98.59 |
| 16 | 84.23 | 1.61 | 22.95 | 23.00 | 96.07 |
| 17 | 82.15 | 0.48 | 13.60 | — | 99.72 |

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A process of the preparation of blanks and dental shaped parts which contain coloring compounds, the process comprising:
   a) coating an oxide powder with a coloring substance in a fluidized bed reactor by using a fluid which contains said coloring substance and a gaseous carrier medium to produce a colored powder,
   b) pressing the colored powder to produce a shaped body, and
   c) sintering the compressed shaped body.

2. The process according to claim 1, further comprising grading the colored powder, and adding the graded colored powder to a compression mold.

3. The process according to claim 1, further comprising after step a), coating at least one further uncolored oxide powder with at least one further coloring substance, and successively filling the further colored oxide powder into a compression mold.

4. The process according to claim 1, wherein aqueous solutions of coloring metal salts of d- or f-elements of the periodic table are used as coloring substances.

5. The process according to claim 1, wherein nitrate hydrates or chloride hydrates are used as coloring substances.

6. The process according to claim 1, wherein $Pr(NO_3)_3 \cdot 5H_2O$, $Fe(NO_3)_3 \cdot 9\,H_2O$, $Tb(NO_3)_3 \cdot 5\,H_2O$ or $CrCl_3 \cdot 6\,H_2O$ are used as coloring substances.

7. The process according to claim 1, wherein the coloring substances are dissolved in water with a water-soluble binder and homogenized.

8. The process according to claim 1, wherein the oxide powders comprise $ZrO_2$.

9. The process according to claim 1, wherein the oxide powders are doped with stabilizing oxides of Ce, Y, Al, Ca and/or Mg.

10. The process according to claim 1, wherein step b) takes place at pressures of 50 to 500 MPa.

11. The process according to claim 1, wherein the powder or powders of the oxide ceramic are colored before pressing.

12. The process according to claim 1, further comprising pre-sintering the shaped body before step c) to form a pre-sintered blank.

13. The process according to claim 12, wherein the shaped body is pre-sintered at a temperature of 800 to 1300° C. to produce the blank.

14. The process according to claim 13, wherein the duration of the pre-sintering process is 1 to 4 hours.

15. The process according to claim 12, further comprising subjecting the pre-sintered blank to a material-removing process and to dense-sintering at a temperature of 1200 to 1600° C.

16. The process according to claim 15, wherein the duration of the dense sintering is 5 minutes to 2 hours.

17. The process according to claim 1, wherein the oxide powder comprises 98.0 to 99.9999 wt.-% of nanoscale $ZrO_2$ powder.

18. The process according to claim 17, wherein the nanoscale $ZrO_2$ powder has a specific surface area of $\geq 100$ $m^2/g$ and contains 0.0001 to 2 wt.-% of another oxide component.

19. The process according to claim 18, wherein the other oxide component comprises a $ZrO_2$ compound with a specific surface area <100 m²/g, a colored $ZrO_2$ compound or a coloring oxide or a mixture of coloring oxides.

20. The process according to claim 12, further comprising subjecting the pre-sintered blank to a material-removing process and to dense-sintering at a temperature of 1000 to 1250° C.

21. The process according to claim 1, wherein the oxide powder is a composition based on $ZrO_2$, the composition comprising the following components:
Pr, calculated as $Pr_2O_3$,
Fe, calculated as $Fe_2O_3$,
Tb, calculated as $Tb_2O_3$, and
Mn, calculated as $Mn_2O_3$,
in a total quantity of 0.0001 to 0.75 wt.-%.

22. The process according to claim 21, wherein the oxide powder contains the components in a total quantity of 0.0001 to 0.6 wt.-%.

23. The process according to claim 22, wherein the oxide powder contains the components in a total quantity of 0.0004 to 0.37 wt.-%.

24. The process according to claim 21, wherein the oxide powder comprises the components in the following quantities, in wt. %:

| | |
|---|---|
| Pr, calculated as $Pr_2O_3$ | 0.0001-0.01 |
| Fe, calculated as $Fe_2O_3$ | 0.005-0.5 |
| Tb, calculated as $Tb_2O_3$ | 0.0001-0.1 |
| Mn, calculated as $Mn_2O_3$ | 0.0001-0.1. |

25. The process according to claim 1, wherein the average grain diameter is 1 to 100 μm.

26. The process according to claim 1, wherein the average grain diameter is 30 to 80 μm.

* * * * *